(12) United States Patent
Scheltes

(10) Patent No.: US 11,141,181 B2
(45) Date of Patent: Oct. 12, 2021

(54) SURGICAL INSTRUMENT

(71) Applicant: DEAM HOLDING B.V., Amsterdam (NL)

(72) Inventor: Julien Serge Scheltes, Amsterdam (NL)

(73) Assignee: DEAM HOLDING B.V., Amsterdam (NL)

( * ) Notice: Subject to any disclaimer, the term of this patent is extended or adjusted under 35 U.S.C. 154(b) by 574 days.

(21) Appl. No.: 15/758,608

(22) PCT Filed: Sep. 7, 2016

(86) PCT No.: PCT/NL2016/050623
§ 371 (c)(1),
(2) Date: Mar. 8, 2018

(87) PCT Pub. No.: WO2017/043969
PCT Pub. Date: Mar. 16, 2017

(65) Prior Publication Data
US 2018/0280048 A1    Oct. 4, 2018

(30) Foreign Application Priority Data

Sep. 10, 2015  (NL) ..................................... 2015423

(51) Int. Cl.
| | | |
|---|---|---|
| *A61B 17/29* | (2006.01) | |
| *A61B 34/00* | (2016.01) | |
| *A61B 17/00* | (2006.01) | |

(52) U.S. Cl.
CPC .......... *A61B 17/2909* (2013.01); *A61B 17/29* (2013.01); *A61B 34/71* (2016.02); *A61B 2017/00424* (2013.01)

(58) Field of Classification Search
CPC ......... A61B 34/70; A61B 37/71; A61B 34/30; A61B 17/29; A61B 2017/291;
(Continued)

(56) References Cited

U.S. PATENT DOCUMENTS 5,176,696 A    1/1993  Saunders
5,441,494 A *  8/1995  Ortiz .......................... B25J 3/00
                                                        294/213
(Continued)

FOREIGN PATENT DOCUMENTS

ES    2 319 954 A1    5/2009
WO    2014/053652 A1   4/2014

OTHER PUBLICATIONS

International Search Report, dated Jan. 9, 2017, from corresponding PCT/NL2016/050623 application.

*Primary Examiner* — Dianne Dornbusch
(74) *Attorney, Agent, or Firm* — Nixon & Vanderhye

(57) ABSTRACT

Disclosed is a surgical instrument with an elongate body with a longitudinal axis having a distal end and a proximal end. The instrument has a pitch capstan having an axis transversely to the longitudinal axis at one end of the elongate body. At least two pairs of cables extend along the elongate body, along the pitch axis to a respective work member to which they are attached. The cables are guided in sliding contact along a slide bearing situated at or near the pitch axis. Also disclosed is a handle for a medical instrument having a hinging connection with the elongate body situated near an inside hand region of the user.

20 Claims, 16 Drawing Sheets

(58) Field of Classification Search
CPC .... A61B 2017/2911; A61B 2017/2912; A61B 2017/2925; A61B 2017/2927; A61B 2017/2929; A61B 2017/003; A61B 2017/00318; A61B 2017/00323; A61B 2017/00327; A61B 2017/0042; A61B 2017/00424; A61B 2017/00438; A61B 2017/00442; A61B 2017/00845; A61B 2017/2919; A61B 2017/2924; A61B 2034/715; A61B 2034/301; A61B 2034/305; A61B 2034/306; A61B 17/2909

See application file for complete search history.

(56) References Cited

U.S. PATENT DOCUMENTS

| | | | |
|---|---|---|---|
| 5,797,900 A | 8/1998 | Madhani et al. | |
| 5,976,121 A * | 11/1999 | Matern | A61B 17/2909 606/1 |
| 6,024,748 A * | 2/2000 | Manzo | A61B 17/11 206/340 |
| 6,432,112 B2 * | 8/2002 | Brock | A61B 34/70 606/130 |
| 2002/0040217 A1 | 4/2002 | Jinno | |
| 2007/0208375 A1 * | 9/2007 | Nishizawa | A61B 34/71 606/205 |
| 2009/0112230 A1 | 4/2009 | Jinno | |
| 2010/0004663 A1 | 1/2010 | Murphy et al. | |
| 2010/0011900 A1 | 1/2010 | Burbank | |
| 2012/0095298 A1 * | 4/2012 | Stefanchik | A61B 17/2909 600/219 |
| 2012/0143173 A1 * | 6/2012 | Steege | A61B 17/29 606/1 |
| 2012/0277762 A1 * | 11/2012 | Lathrop | A61B 34/70 606/130 |
| 2014/0318288 A1 * | 10/2014 | Lee | F16H 19/06 74/89.2 |
| 2015/0073434 A1 | 3/2015 | Simaan et al. | |
| 2015/0265262 A1 * | 9/2015 | Dewaele | A61B 17/00234 606/1 |
| 2016/0184040 A1 * | 6/2016 | Sholev | A61B 17/2909 606/130 |
| 2018/0000550 A1 * | 1/2018 | Beira | A61B 34/71 |

* cited by examiner

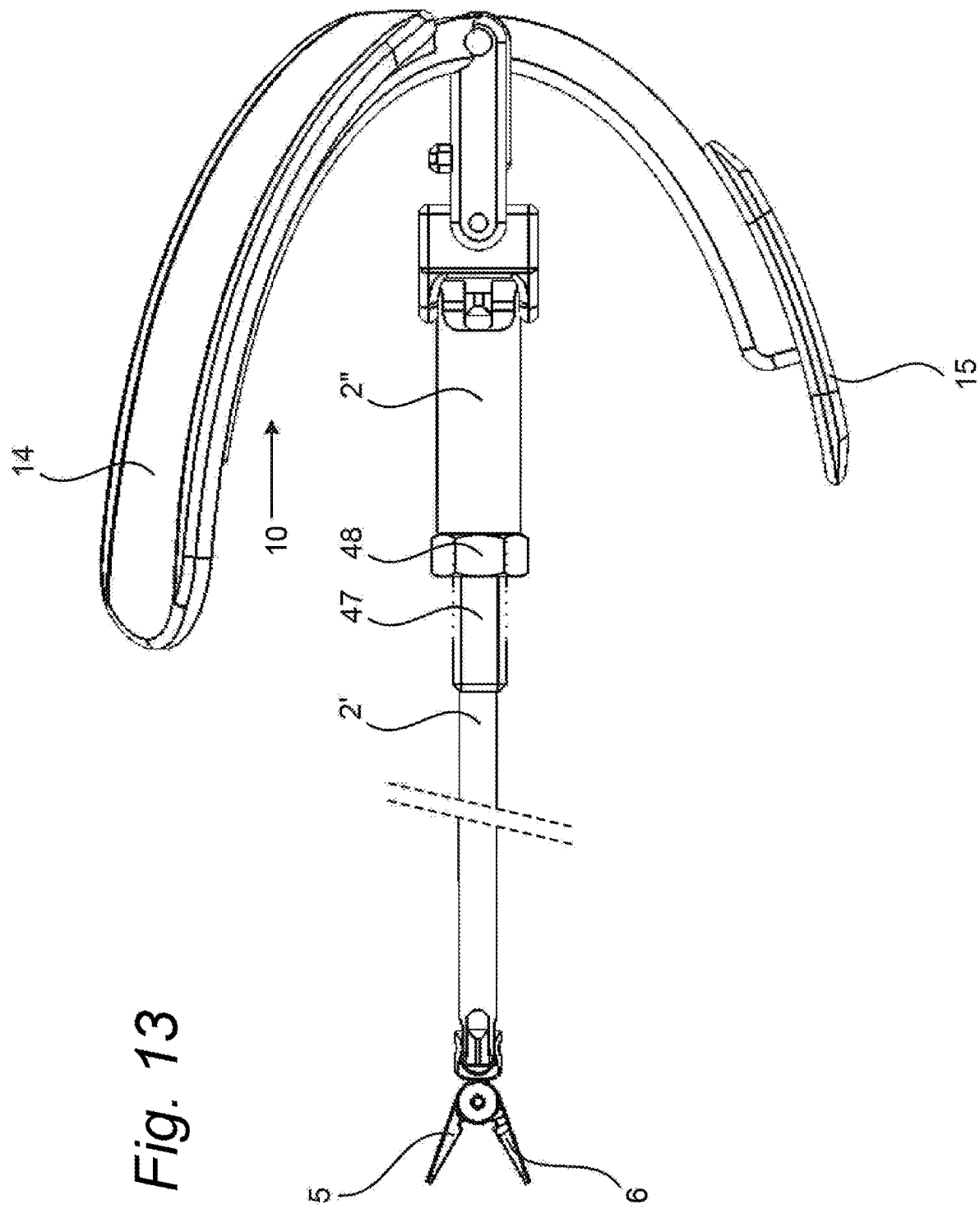

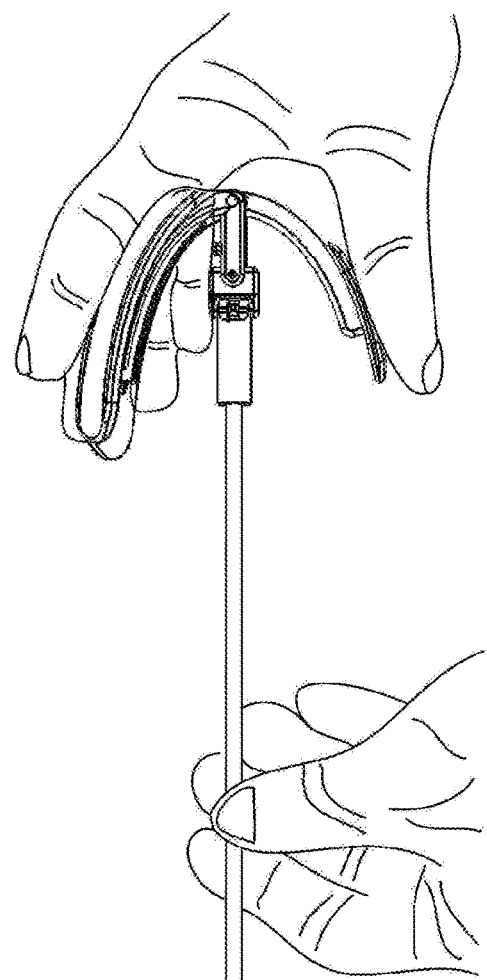
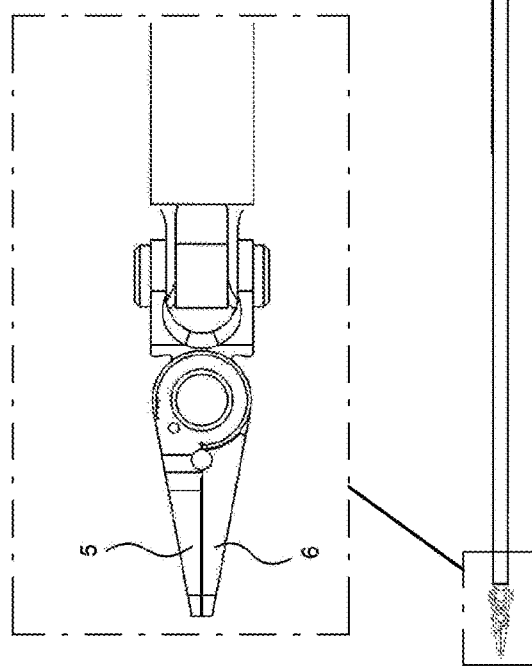
Fig. 14

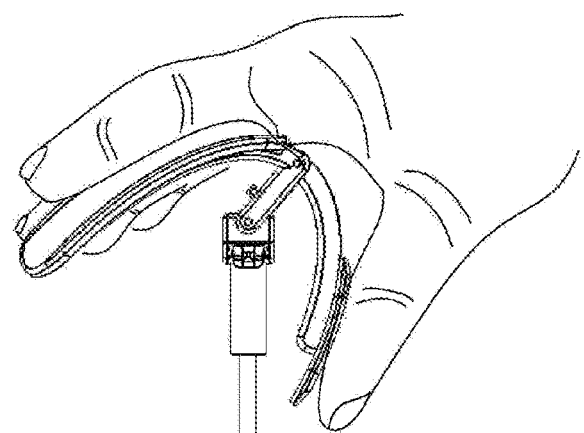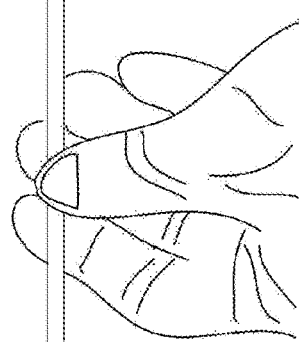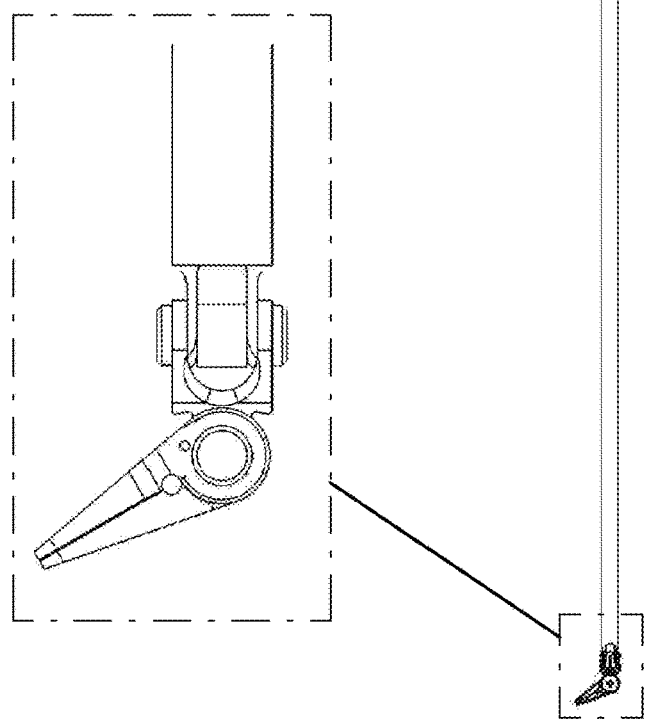
Fig. 16

SURGICAL INSTRUMENT

FIELD OF THE INVENTION

The invention relates to a surgical instrument comprising an elongate body with a longitudinal axis having a distal end and a proximal end, a pitch capstan having an axis transversely to the longitudinal axis at one end of the support member and a support rotatably mounted on the pitch capstan, the support carrying a transverse capstan having an axis transversely to the longitudinal axis and to the pitch axis, and two work members movable relative to one another around the transverse axis connected to the support member, two pairs of cables extending along the elongate body, along the pitch axis to a respective work member to which they are attached.

The invention also relates to an improved handle for a surgical instrument.

BACKGROUND OF THE INVENTION

Such an instrument is known from U.S. Pat. No. 5,797,900 in which a laparoscopic device is described having at the distal end of the elongate support a pair of working tools such as clamps, graspers, scissors or staplers. The working tools are actuated by two continuous cable loops that are each guided to a respective working tool via idler pulleys that can rotate around the pitch axis. The cables are operated by a series of drive motors that are under the control of a surgeon at a remote location. The known cable drive comprising idler pulleys results in a relatively complex construction and in a relatively large volume of the instrument.

It is an object of the invention to provide a surgical instrument which is of simple construction and which has a reduced number of components. It is a further object of the invention to provide a surgical instrument having reduced dimensions. It is furthermore an object of the invention to provide a surgical instrument that can be easily operated and manipulated by a surgeon at an on site location.

SUMMARY OF THE INVENTION

Hereto a surgical instrument according to the invention is characterized in that the cables are guided in sliding contact along a slide bearing situated at or near the pitch axis.

It was found that the known idler pulleys can effectively be replaced by sliding contact of the cables at or near the pitch axis while maintaining the instrument's dexterity and accurate force reflection. Hereby the number of components can be reduced so that the construction of the device is simplified and made more cost effective. This is especially important when producing the instrument as a disposable device, suitable for single use only.

Furthermore, by the use of a slide bearing instead of the known idler pulleys, the size of the instrument especially at the distal end can be reduced by several mm, which is important when utilizing the device in minimally invasive operations, in which the device is inserted into the abdominal cavity via a cannula.

In particular, the present invention results in a reduced distance between the slide bearing and the transverse capstan carrying the work members at the distal end, hence providing a compact construction.

As used herein, the "distal end" of the surgical instrument is the side which is intended to come into contact with a patient and carries work members in the form of a tool such as clamps, graspers, scissors or staplers. With the term "proximal end" the side of the instrument carrying the handle of the device is indicated that is acted on by a user, such as a surgeon. At the proximal end, the work members have the form of grips that can be acted on by the fingers of the user. The slide bearing according to the invention can be situated at the distal end, at the proximal end or at both ends of the surgical instrument.

In an embodiment of a surgical instrument according to the invention, the slide bearing comprises the pitch capstan. The surface of the capstan, which is made of a metal such as surgical grade stainless steel, forms a slide bearing along which the steel cables of the cable loop can move with little friction. The material of the capstan can comprise a stainless steel tube with a low friction coating or shrink tube material. The material of the capstan can in an alternative embodiment be formed of a low friction plastic, such as PTFE or FEP.

In a preferred embodiment of a surgical instrument according to the invention, the cables of a pair of connected cables cross from one side of the lateral plane defined by the longitudinal axis and the pitch axis to the other side of said plane, when going from a position on the elongate body to a position on the work member. By pulling both top and bottom cable of each cable loop, the work tool can be pivoted around the pitch axis in an accurately controlled manner while the cables slide crosswise along the surface of the capstan. The moment exerted by the cables on the work members is substantially constant and the cables remain accurate aligned along the pitch capstan.

In a further embodiment of a surgical instrument according to the invention, the pitch capstan comprises a bushing being laterally displaceable relative to the pitch axis. Displacement of the pitch capstan helps in compensating small undesired movements on the proximal side from being transferred to the work members at the distal side.

A further embodiment of a surgical instrument according to the invention has a slide bearing that comprises a block having a central passage extending around the pitch axis and on each side of the lateral plane defined by the longitudinal axis and the pitch axis two cable passages extending in the direction of the longitudinal axis. In this manner a simple and compact bearing is provided which can be accommodated to only occupy a small volume around the pitch axis. The use of a bearing block allows for the work members to be deflected through relatively large angles around the pitch axis, such as a 90 degree bend, while the bearing block is deflected through smaller angles, such as 45 degrees, hence limiting the angle of deflection of the cables guided by the bearing.

In again another embodiment of a surgical instrument according to invention, the pitch axis is situated at a proximal end of the support member, the work members comprising a handle member with thumb and finger grips defining a gripping area having a finger tip region for supporting end parts of the fingers of a user and an inside hand region near the joint of fingers and thumb of a user, the pitch axis being situated nearer to the inside hand region than to the finger tip region when seen along the longitudinal axis.

The handle according to the invention provides accurate control of the work members at the distal end by the handle member having the upper and lower finger grips mutually connected to the proximal pitch axis in a position that is close to the joint of thumb and index finger of a user. The position of the proximal pitch axis to the user's natural joints for pinching with the index finger, for operation of for instance jaw movements at the distal end, and to the wrist for pitch movements, provides for an accurate and intuitive control of the work members.

In a further embodiment, the support member comprises a tensioning device for displacing the pitch axis along the longitudinal axis. This allows transport and storage of the surgical instrument at reduced tension in the drive cables, which can in that way better maintain their accurately defined operational characteristics and prevents the plastic materials and the cables from being subject to deformations.

The handle may comprise the first and second members that are attached to the proximal end of the elongate body via an arm extending from the hinge point to the transverse axis.

The handle forms an arcuate support for the thumb and fingers and can be pivoted around the proximal transverse hinge axis by the user for moving the tip at the distal end up or down around the distal transverse axis.

In a preferred embodiment, the finger support part comprises an index finger support part and situated adjacent thereto an additional finger support part for supporting at least one further finger. The handle according to the invention provides a steady and secure support for the hand of the user and allows accurate manipulation of the distal end.

BRIEF DESCRIPTION OF THE DRAWINGS

Some embodiments of a surgical instrument according to the invention will by way of non-limiting example be described in detail with reference to the accompanying drawings. In the drawings:

FIG. 13 shows an enlarged detail of a cable tensioning mechanism, and FIGS. 14-18 show the operational positions of the hand of a user of the medical device upon pinching and steering of the distal end of the surgical instrument.

DETAILED DESCRIPTION OF THE INVENTION

Figure 1:
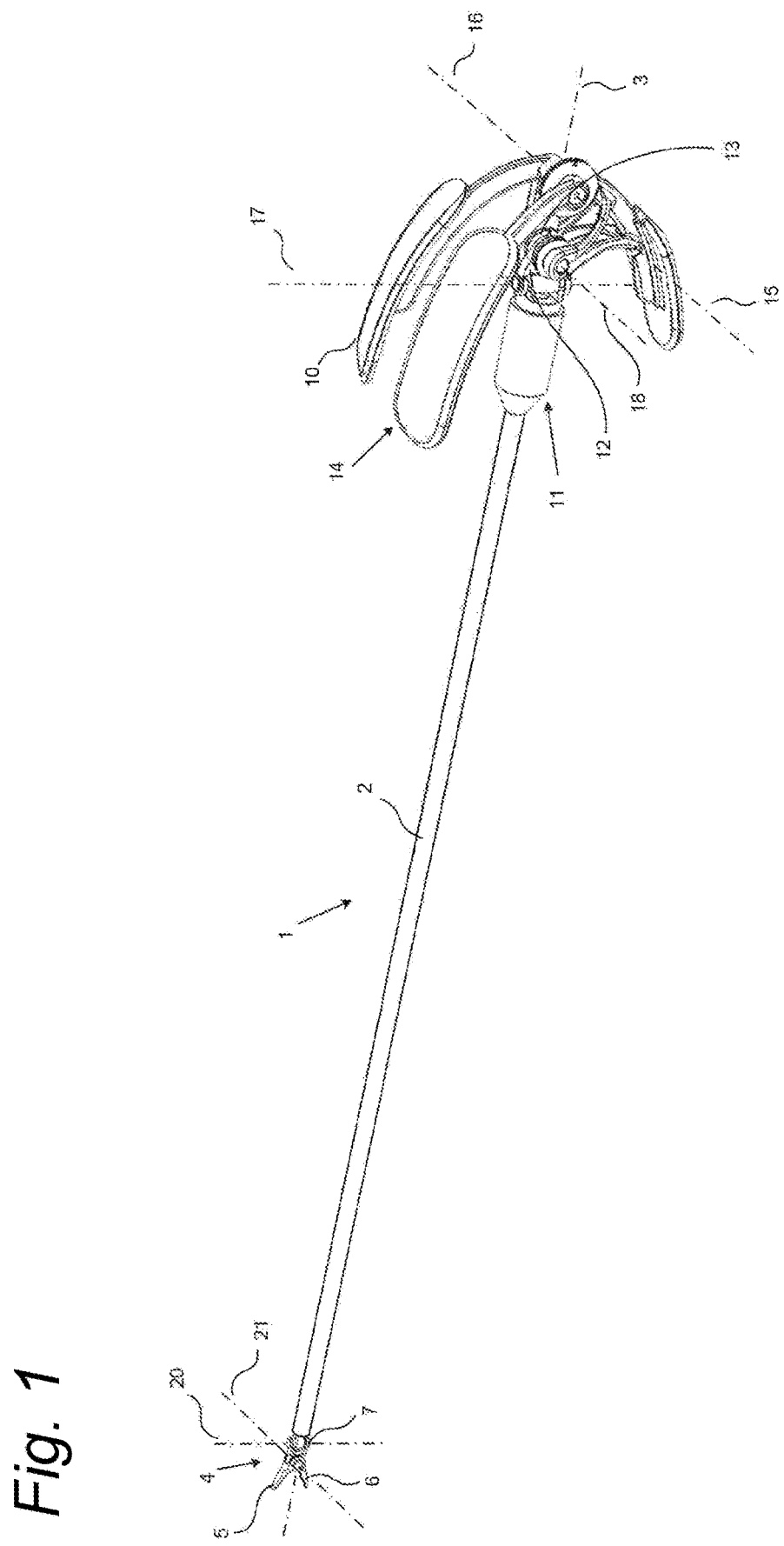
FIG. 1 shows a perspective view of a surgical instrument according to the invention.

FIG. 1 shows a perspective view of a surgical instrument 1 according to the invention, that in this embodiment is formed by laparoscopic device. The instrument 1 comprises a hollow shaft 2 with a longitudinal axis 3. At a distal end 4 of the shaft 2, work members, that are in this exemplary embodiment in the form of a pair of jaws 5, 6 are connected to a distal support member 7 (see FIG. 3). The distal support member 7 and the jaws 5,6 are connected via cables that extend within the shaft 2, to a handle 10 at a proximal end 11 of the instrument 1. The support member 7 can pivot around a distal pitch axis 20 and the jaws 5,6 can pivot around a distal transverse jaw axis 21.

The handle 10 is carried by a proximal support member 12 that can rotate around a proximal pitch axis 17. The support member 12 carries a pair of pulleys 13 that are connected via respective cable pairs to the jaws 5,6 (see FIG. 5). The pulleys 13 can be rotated around pivot axis 18, that is transverse to the longitudinal axis 3 and to the proximal pitch axis 17.

The handle 10 has an upper finger support part 14 and lower thumb support part 15, the support parts being hingingly interconnected along proximal jaw axis 16.

Figure 2:
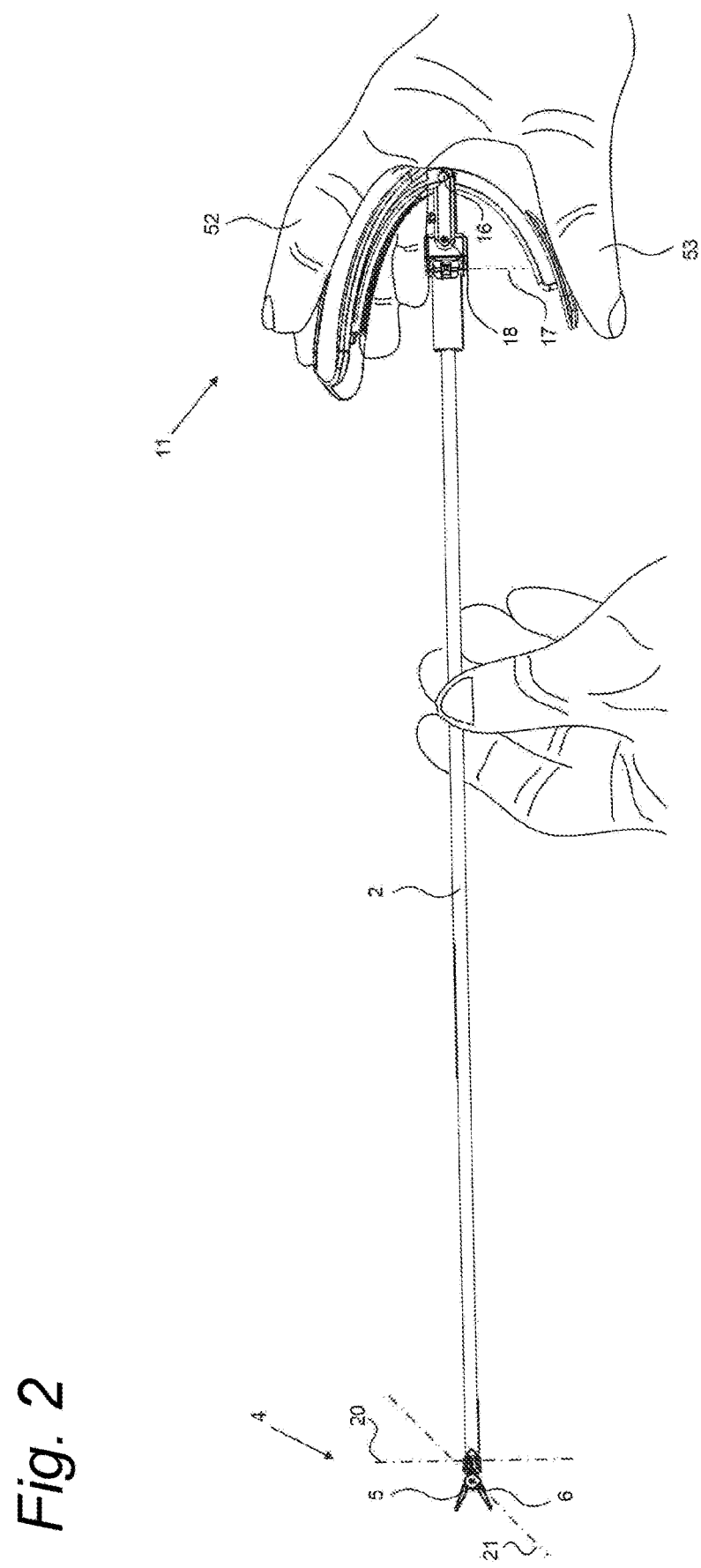
FIG. 2 shows the hand position of a user during manual operation of the surgical instrument of FIG. 1.

FIG. 2 shows the hands of a user gripping the handle 10. When the user pinches together index finger 52 and thumb 53, the finger support part 14 and thumb support part 15 of the handle 10 are pivoted around proximal jaw axis 16. |This causes one of the jaws 5,6 or both jaws to be pivoted around the distal transverse jaw axis 21 relative to the other jaw, to an open or closed position.

Rotating the handle 1 around the proximal pitch axis 17 will pivot the jaws 5,6 jointly, either in opened or closed position, around the distal pitch axis 20.

Pivoting the handle 10 around proximal pivot axis 18 will jointly pivot the jaws 5,6 in either closed or opened position, around the distal transverse jaw axis 21.

Figure 3:
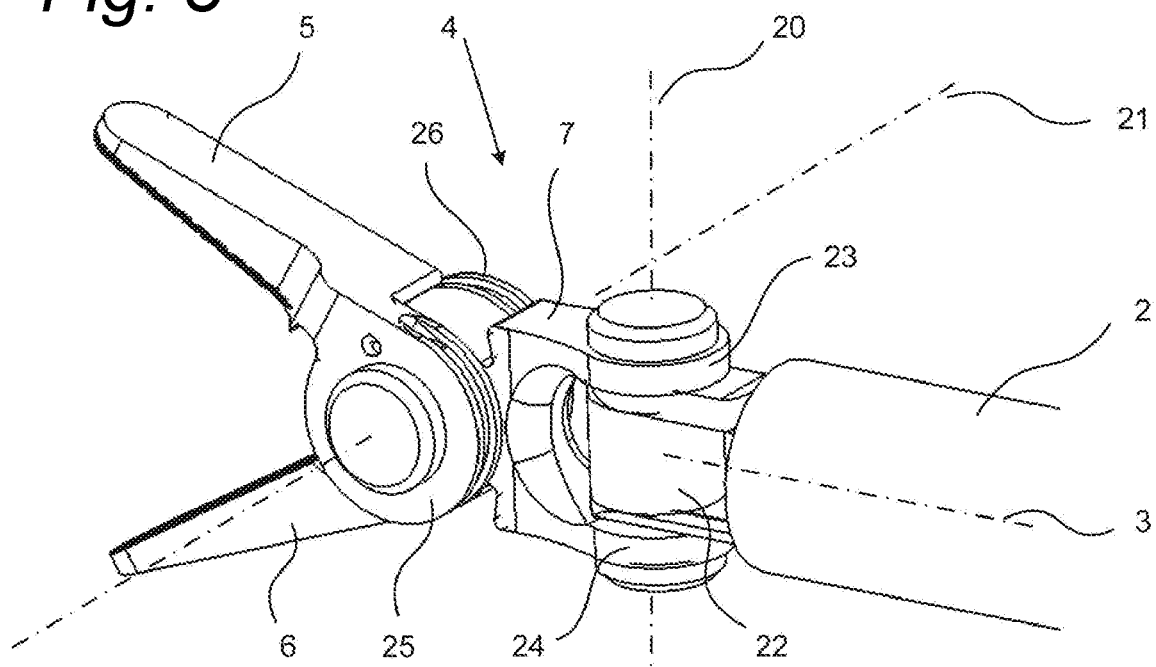
FIG. 3 shows an enlarged detail of the distal end of the surgical instrument of FIG. 2, with omission of the drive cables.

FIG. 3 shows an enlarged detail of the distal end 4 of the medical instrument according to the invention, wherein the support member 7 is formed by a bracket and comprises a cylindrical capstan 22 to which ears 23, 24 of the bracket are attached. Each jaw 5,6 is provided with a respective jaw pulley 25,26 to which the ends of respective cable pairs, shown in FIG. 4, are attached.

Figure 4:
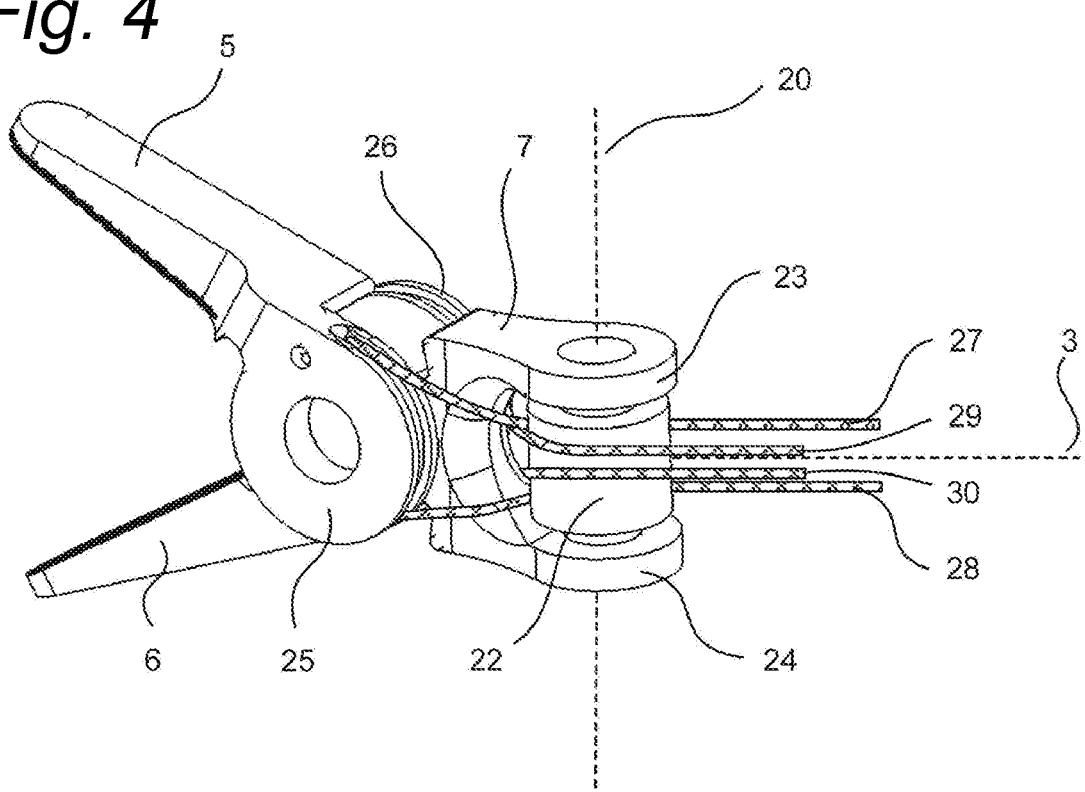
FIG. 4 shows the detail of FIG. 3 including the drive cables.

FIG. 4 shows the cable pairs 27,28 and 29,30 being guided from the shaft 2 along the capstan 22, which forms a slide bearing, to the jaw pulleys 25,26. The cables 27 and 28 cross the plane 33 (see FIG. 5) that is defined by the distal pitch axis 20 and and perpendicular to the distal transverse jaw axis 21, and are with their end parts fixedly connected to the jaw pulley 25. In a similar manner the cables 29,30 are slidingly guided along the capstan 22 in a crosswise manner to be connected to the jaw pulley 26.

Figure 5:
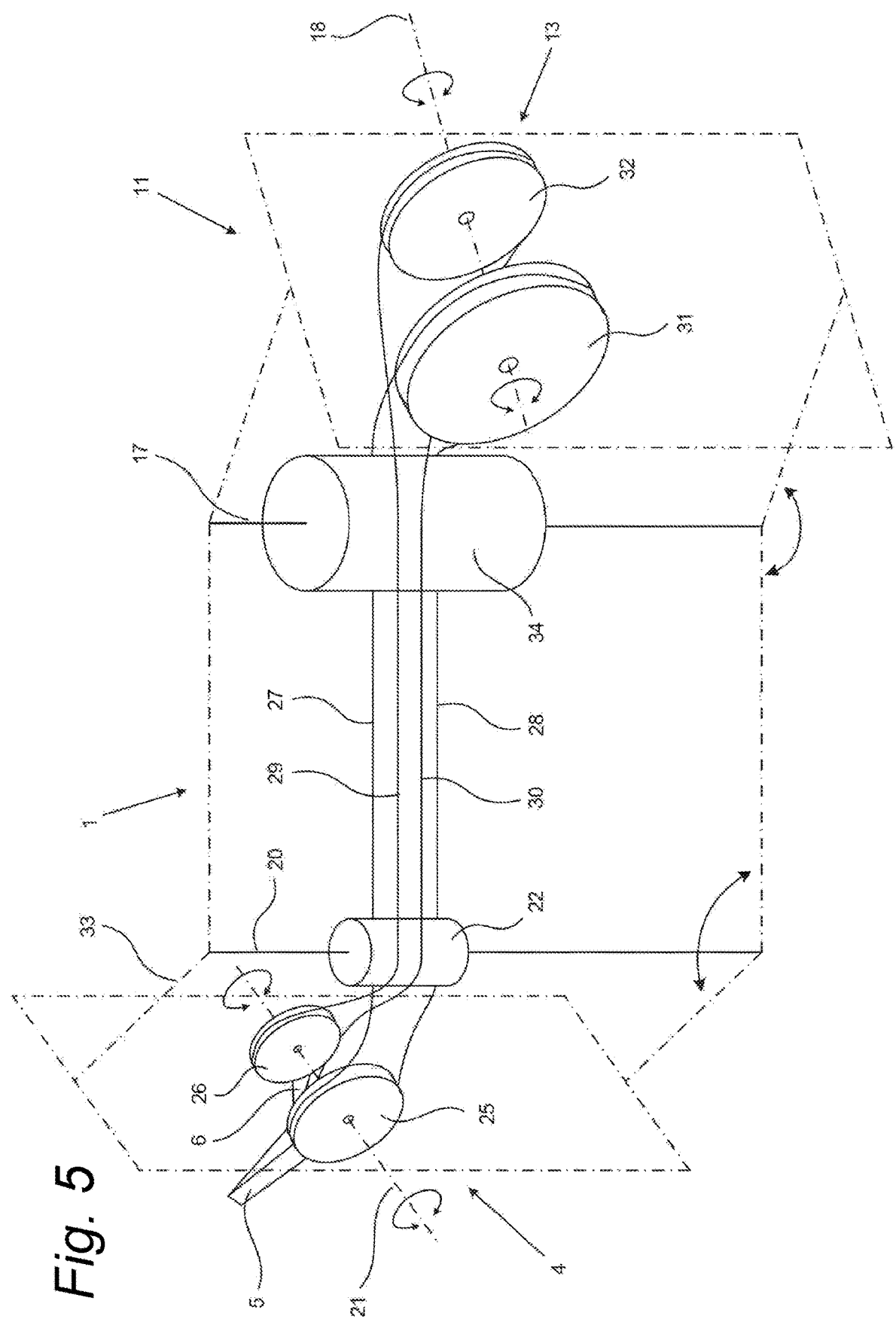
FIG. 5 shows an embodiment of a schematic lay-out of jaws, cables, pulleys and the handle of the medical instrument of FIG. 1.

FIG. 5 shows a schematic view of the cable and pulley lay-out of the medical instrument 1. The end parts of cables 27,28 are connected to jaw pulley 25. The cables 27,28 extend slidingly along distal capstan 22, along proximal capstan 34 and are attached to pinch pulley 31.

The cables 29,30 are at their distal ends connected to the jaw pulley 26 and are guided via distal capstan 22 to the proximal capstan 34, and from there to proximal pivot pulley 32.

The opening and closing of the jaws 5 and 6 is effected by pulling at the cable 27. Pulling at the cable 27 by clockwise rotation of the proximal pinch pulley 31 around proximal pivot axis 18, rotates the jaw pulley 25 to move the jaw 5 away from jaw 6.

The jaws 5,6 are closed to pinch together by pulling on the cable 28 by counter clockwise rotation of the pinch pulley 31 to rotate the jaw pulley 25 to move the jaw 5 into pinching contact with the jaw 6.

The jaws 5,6 can in their pinch position and in their open position, be bent upward together in unison, around the transverse jaw axis 21, by pulling simultaneously at the cables 27 and 29 via simultaneous clockwise rotation of pinch pulley 31 and pivot pulley 32 around the pivot axis 18. Pulling at the cables 28 and 30 will move the jaws 5,6 in unison in a counter clockwise direction around the transverse jaw axis 21. In this manner the tip of the medical device 1 can be steered up or down.

The jaws 5,6 and pulleys 25,26 can be rotated about the distal pitch axis 20 in a clockwise direction by simultaneously pulling at cables 27 and 28 by simultaneous rotation of pulleys 31,32 in a clockwise direction about the proximal pitch axis 17. The jaws 5,6 are rotated about the distal pitch axis 20 in a counter clockwise direction by counter clockwise rotation of the pulleys 31,32 about the proximal axis 17. In this manner the tip of the medical device can be steered to the left or to the right.

Figure 6:
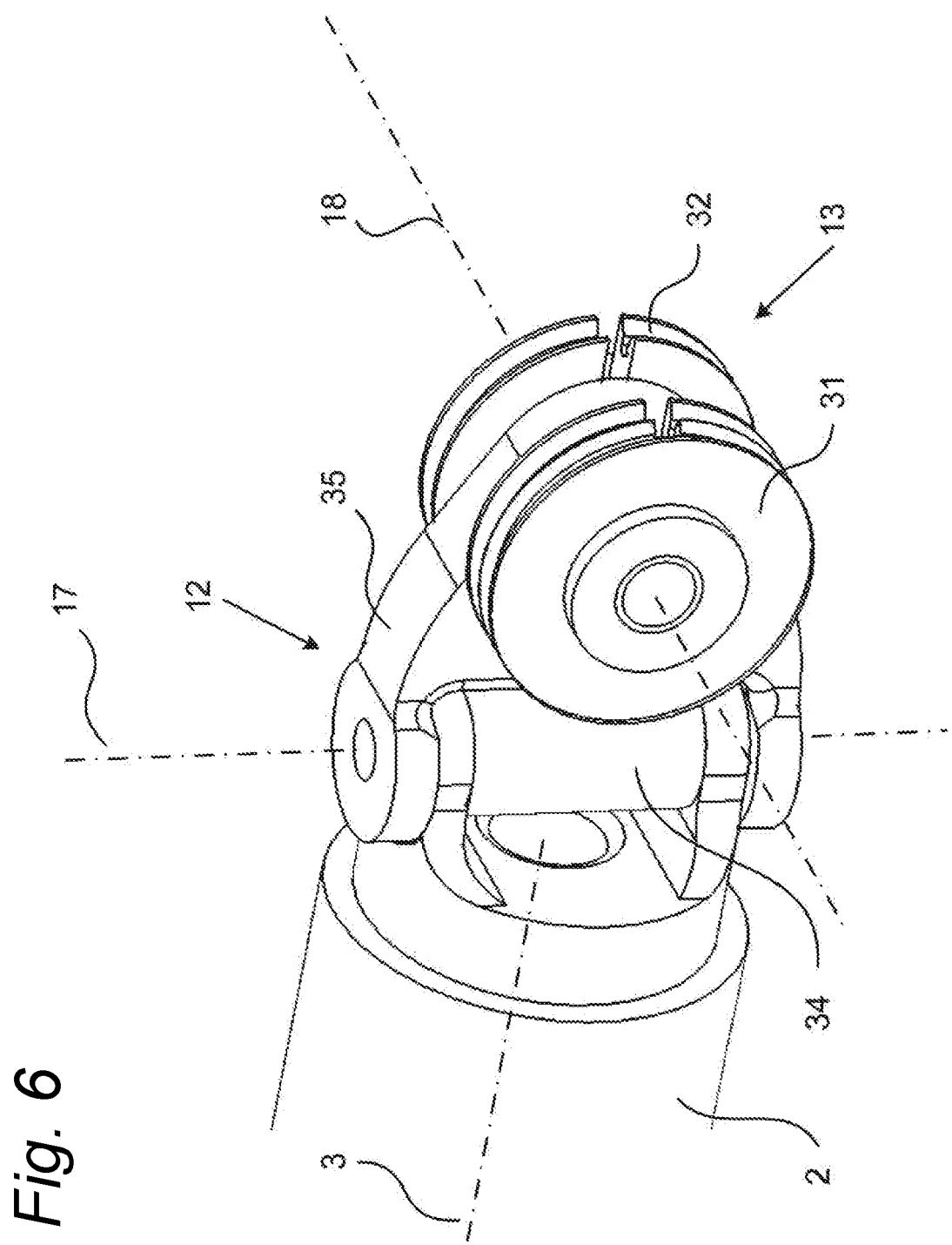
FIG. 6 shows an enlarged detail of the proximal end of the surgical instrument of FIG. 1.

FIG. 6 shows the proximal support member 12 carrying the pair of pulleys 13 comprising the pinch pulley 31 and the pivot pulley 32, that are connected to the proximal capstan 34 via a bracket 35.

Figure 7:
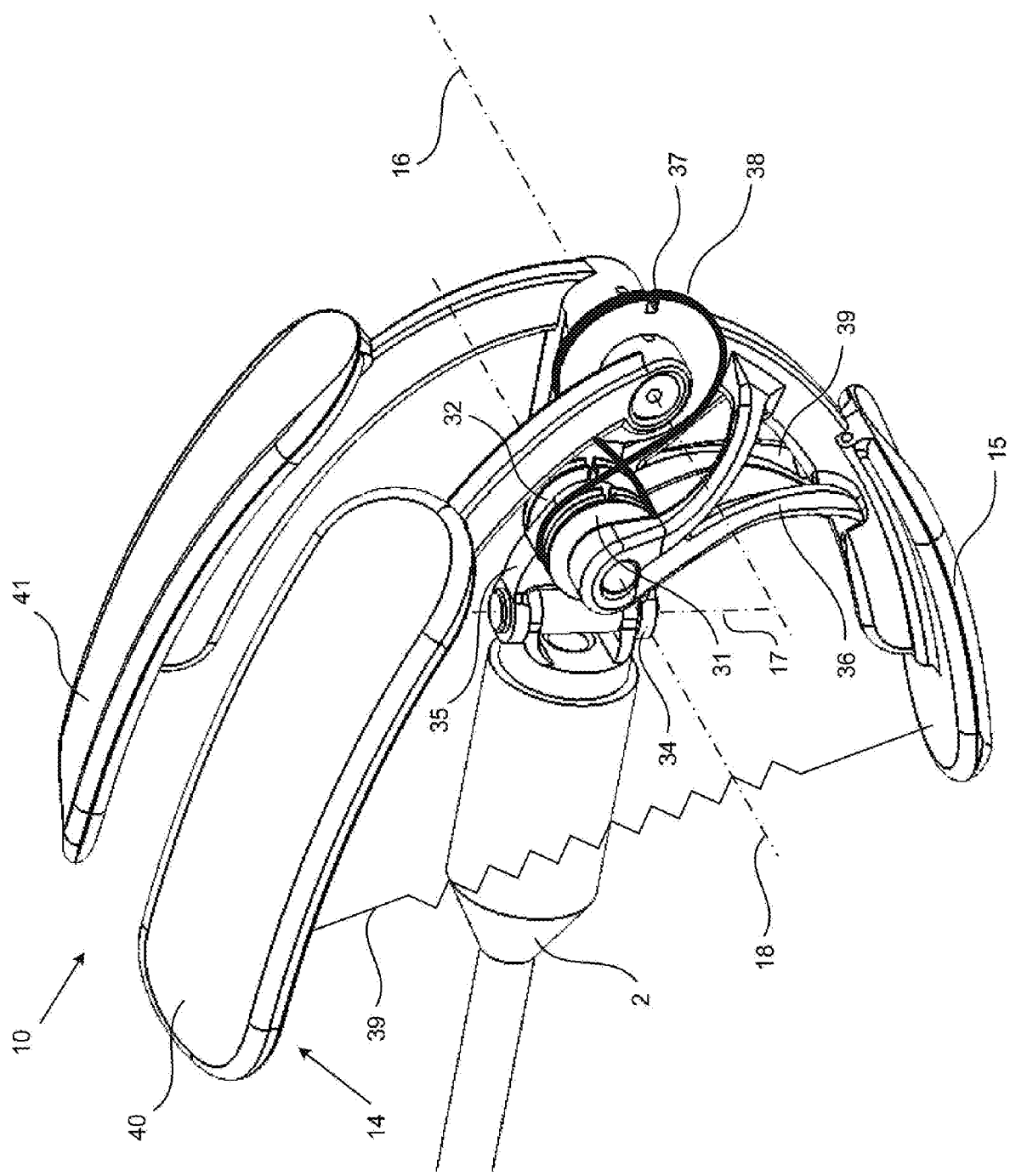
FIG. 7 shows an embodiment of a handle according to the invention.

FIG. 7 shows the handle 10 at the proximal end 11, the upper finger support part 14 and lower thumb support part 15 being interconnected at the position of the proximal jaw axis 16. The upper finger support part 14 comprises an index finger support 40 and an adjacent finger support 41. The adjacent finger support 41 is fixedly connected to the thumb support part 15. The index finger support 40 is attached to a pinch lever 37 and can rotate pinch lever 37 about proximal jaw axis 16. In this embodiment, cable loop 38 extends from the top of the pinch lever 37 to the bottom of the pinch pulley 31 and back. By squeezing the upper finger support part 14 downwards, the cable loop 38 rotates the pinch pulley 31 in a clockwise direction, and the jaws 5,6 at the distal end move to a closed pinching position. Upon release of the squeezing force, a spring member 39 between the lower thumb support part 15 and the index finger support 40, which has been schematically indicated, returns the finger support parts 40, 15 back to a spaced-apart position, such that the pinch pulley 31 rotates in a counter-clockwise direction and the jaws 5,6 are moved apart.

The lower thumb support 15, carrying the pinch lever 37 and the upper finger support part 14, is attached to the bracket 35 via arms 36, 39. Arm 36 is rotatably mounted to axis 18 and pinch pulley 31 and arm 39 is connected to pivot pulley 32. By rotation of the arms 36,39 around the proximal pivot axis 18, the pulleys 31, 32 are rotated in unison so the jaws 5,6 at the distal end are steered in upward or downward direction.

The upper finger support 14 of the handle 10 comprises an index finger support 40 for operation of the pinch movement of the jaws 5,6 and and an adjacent finger support 41 for supporting one or more adjacent fingers of the user for driving the up and down steering of the jaws 5,6. The adjacent finger support 41 is fixedly connected to the thumb support part 15. Joint rotation of the pulleys 31,32 about the proximal pivot axis 18 is effected by the arm 39 being fixedly attached to the pivot pulley 32. Rotation of the finger support parts 15,41 about the axis 18 drives the pivot pulley 32. Upon such rotation, the pinch pulley 31 is driven by the cable 38, as this cable is not displaced when no pinching force is exerted on the index finger support 40.

By operation of the bracket 35 about the proximal pitch axis 17, the pulleys 31,32 are rotated jointly about the pitch axis 17 such that the jaws 5,6 are steered to the left or to the right. The finger supports 40,41 and thumb support 15 are curved to ergonomically fit the fingers of the user. The supports 40,41 can be made of a soft material to provide optimal control of the movement of the jaws 5,6. By providing a separate index finger support 40 and adjacent finger support 41, the pinching movement of the jaws 5,6 and the steering of the jaws in an upward, downward and left or right direction can be independently and accurately controlled by the user.

The free ends of the finger supports 40,41 and 15 define a finger support region and support the tips of the fingers of the user, whereas the pinch lever 37 is situated near an inside hand region of the user where the index finger joins the thumb. Positioning of the proximal pivot axis 18 near the inside hand region of the user provides stable and accurate control of the jaws in all their positions by ergonomic and natural movements of the wrist and fingers of the user. The biasing force exerted by the compression spring 39 ensures continuous and stable contact of the handle 10 with the hand of the user and provides a tactile feedback to the index finger.

It is possible to utilise exchangeable finger supports 15,40,41 to utilise tailor made supports that are adapted to the size of the fingers of the users.

Figure 8:
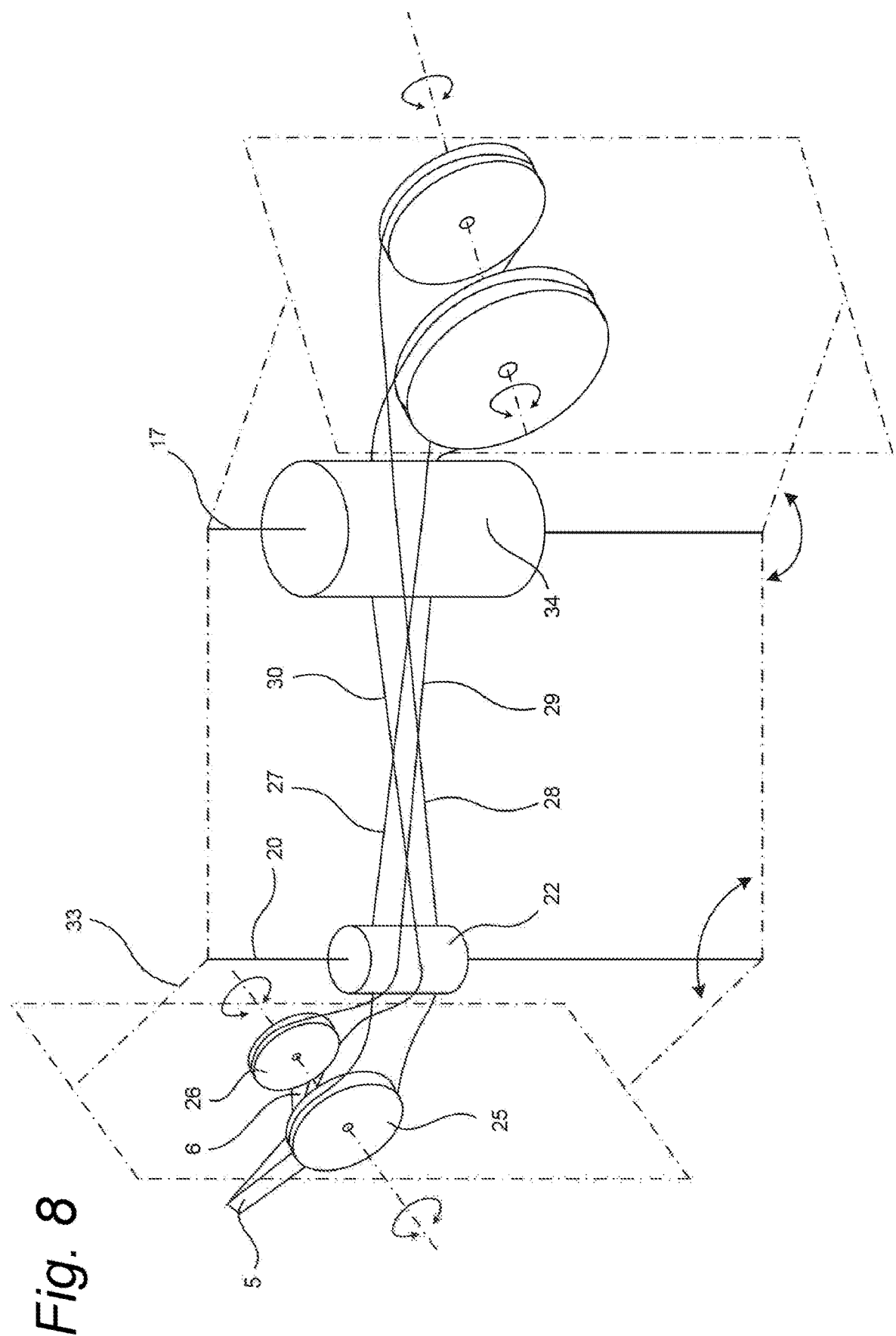
FIG. 8 shows an alternative wherein the cables are crossed at a position between the proximal end and distal end.

In FIG. 8 and alternative embodiment is shown in which the cables 27,28 and 28,29 cross at a position along the body 2 of the instrument, so that operation of the handle 10 mirrors the movement of the jaws 5,6 compared to the embodiment shown in FIG. 5. By varying the diameter of the capstans 22,24, the points of intersection of the cables 27-29 along the longitudinal axis 3 can be adjusted.

Figure 9:
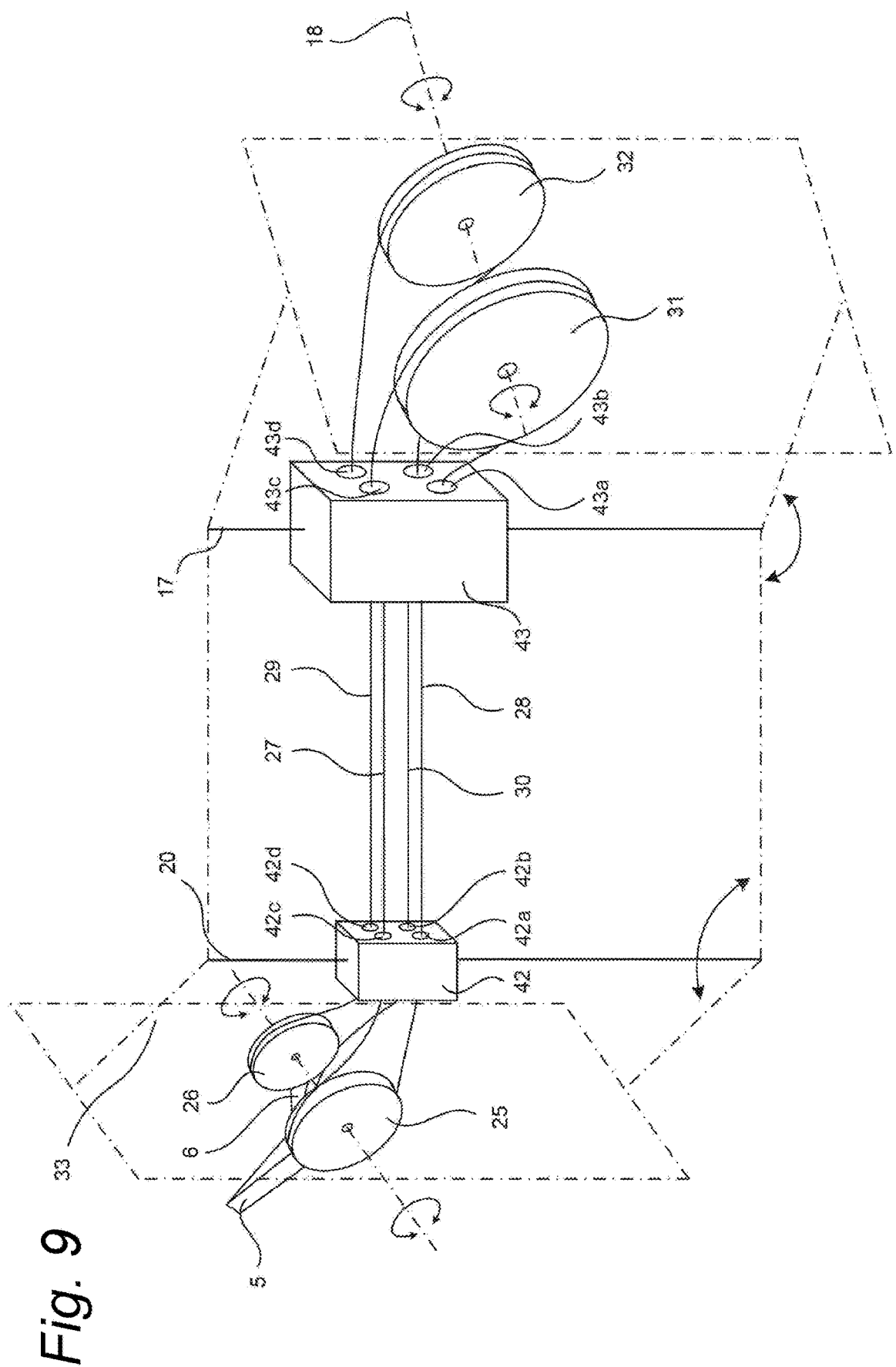
FIG. 9 shows a schematic view of an embodiment of a surgical instrument comprising a slide block.

In FIG. 9 an embodiment is shown in which the capstans 22,34 have been replaced by slide bearings in the form of bearing blocks 42,43, each provided with four passages 42a-42d and 43a-43d for guiding of the cables 27-30. The bearing blocks can rotate around the pitch axes 17, 20.

Figure 10:
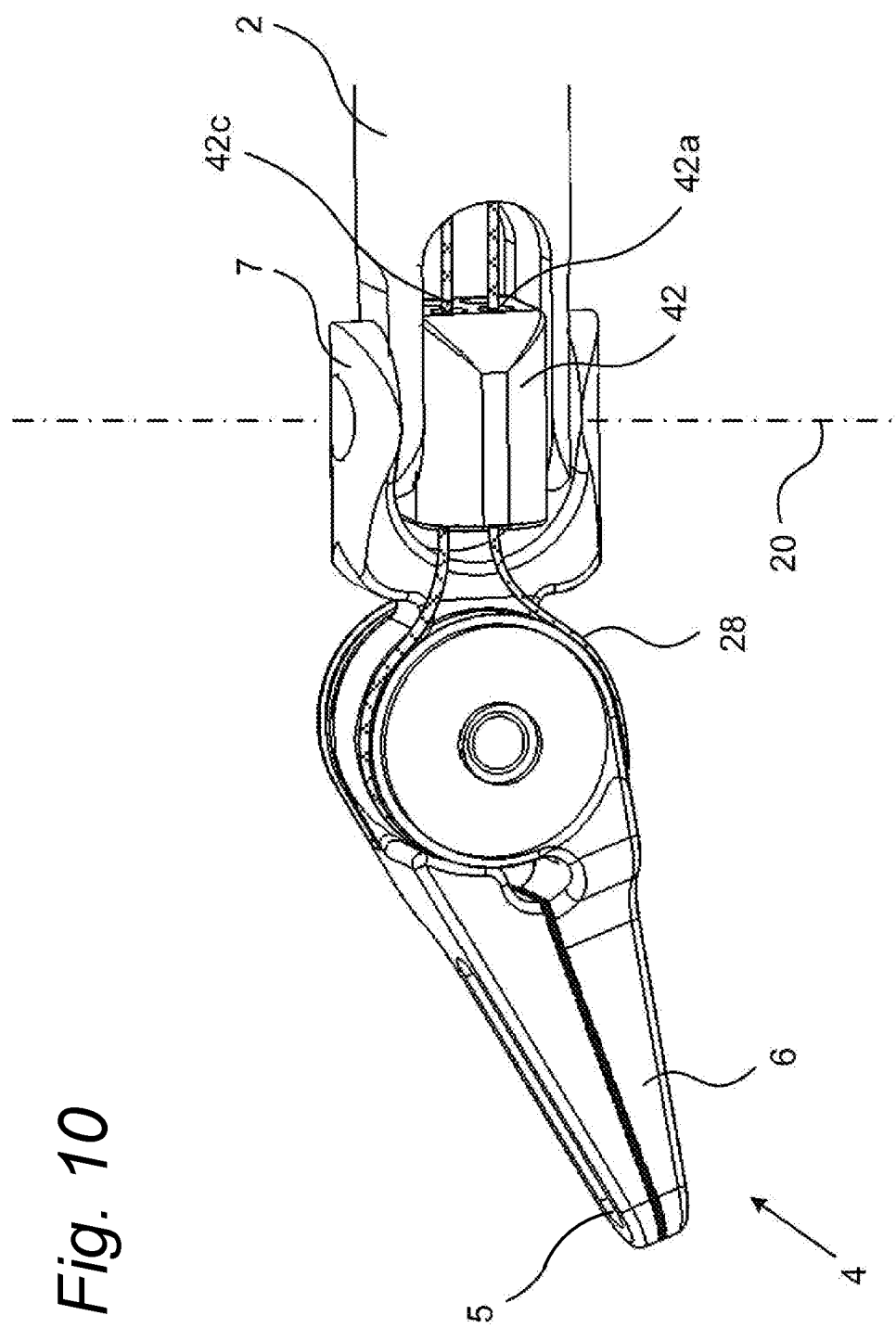
FIG. 10 shows an enlarged detail of the distal end of a surgical instrument comprising a slide bearing block.
Figure 11:
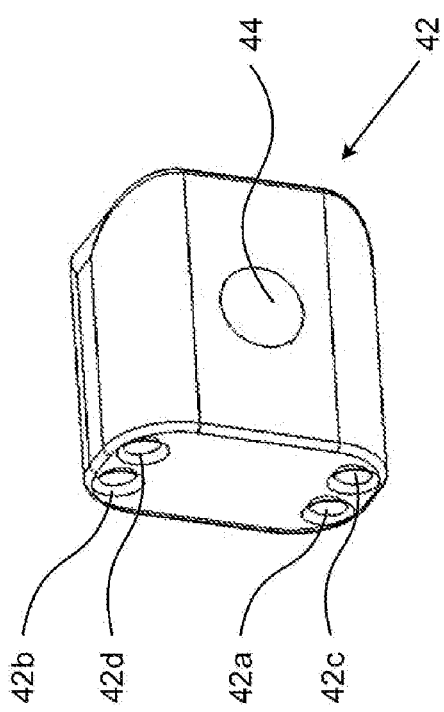
FIG. 11 shows a detail of a slide bearing block having cable passages.

In FIG. 10 the distal end 4 of an embodiment of the medical apparatus is shown comprising a slide bearing block 42 which is fitted within the bracket-shaped support member 7. The cables 27, 28 extend through longitudinal passages 42a, 42c in the block 42. As can be seen in FIG. 11, the block 42 is of a compact design and comprises four longitudinal passages 42a-42d and a central opening 44 for fitting around the distal or proximal capstans 22, 34.

Figure 12C:
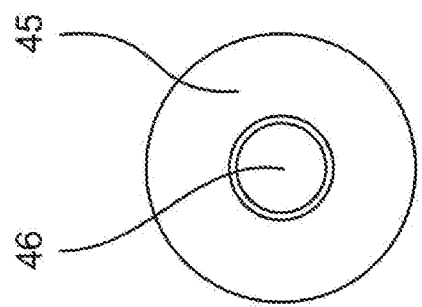
FIG. 12a-12c show embodiments of a capstan having a fixed position, having a variable axial and radial position and having a variable axial position.
Figure 12B:
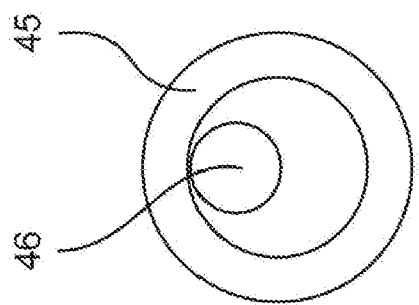
Figure 12A:
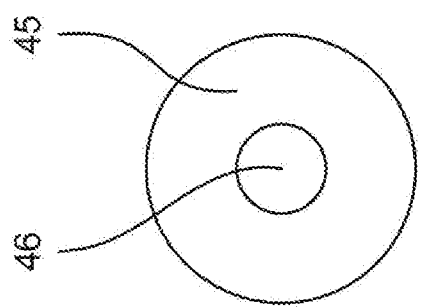

FIG. 12a shows an embodiment of a proximal or distal capstan 45 being of integral form and comprising a metal bushing rotating without play around central pitch axis 46. FIG. 12b shows an embodiment of a capstan 45 which is provided with play rotatable and translatable about pitch axis 46. FIG. 12c shows an embodiment in which an outer metal or plastics tube segment 45 is slidingly placed about pitch axis 46.

FIG. 13 shows a pretensioning mechanism in which the distal end 2' of the shaft 2 is connected to the proximal end 2" via a threaded connection 47,48. In this way the distance of the jaws 5,6 from the handle 10 can be varied and the tension on the cables 27-30 running through the shaft 2 can be adjusted.

FIG. 14 shows operation of the medical instrument for placing the jaws 5,6 of the tip in an pinching position by squeezing on the finger supports between the user's thumb and index finger and placing the jaws 5,6 in a spaced apart position by releasing the pinching force.

Figure 15:
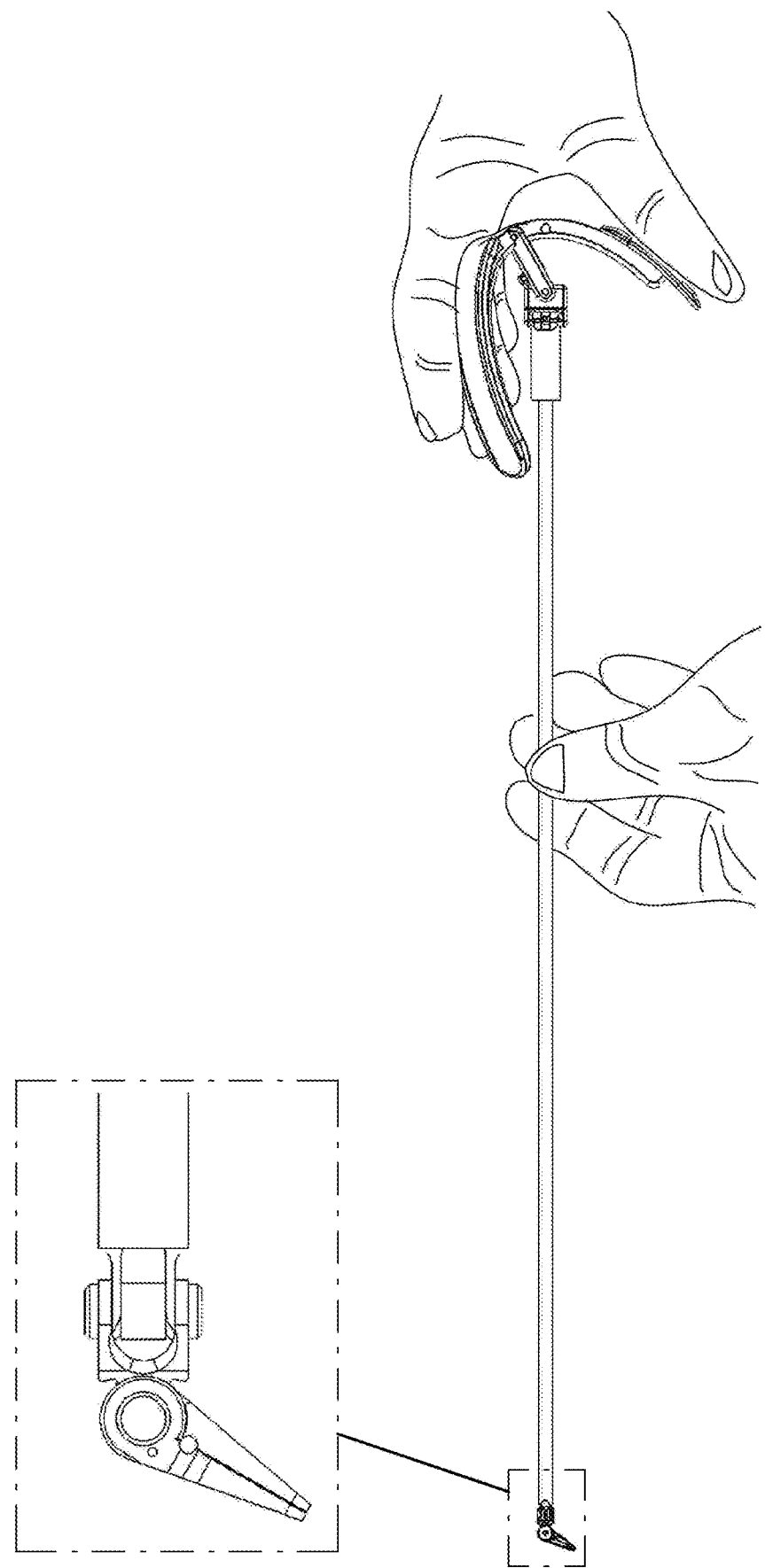

FIG. 15 shows the wrist movement of the user for downward rotation and FIG. 16 for upward rotation of the tip comprising jaws 5,6

Figure 17:
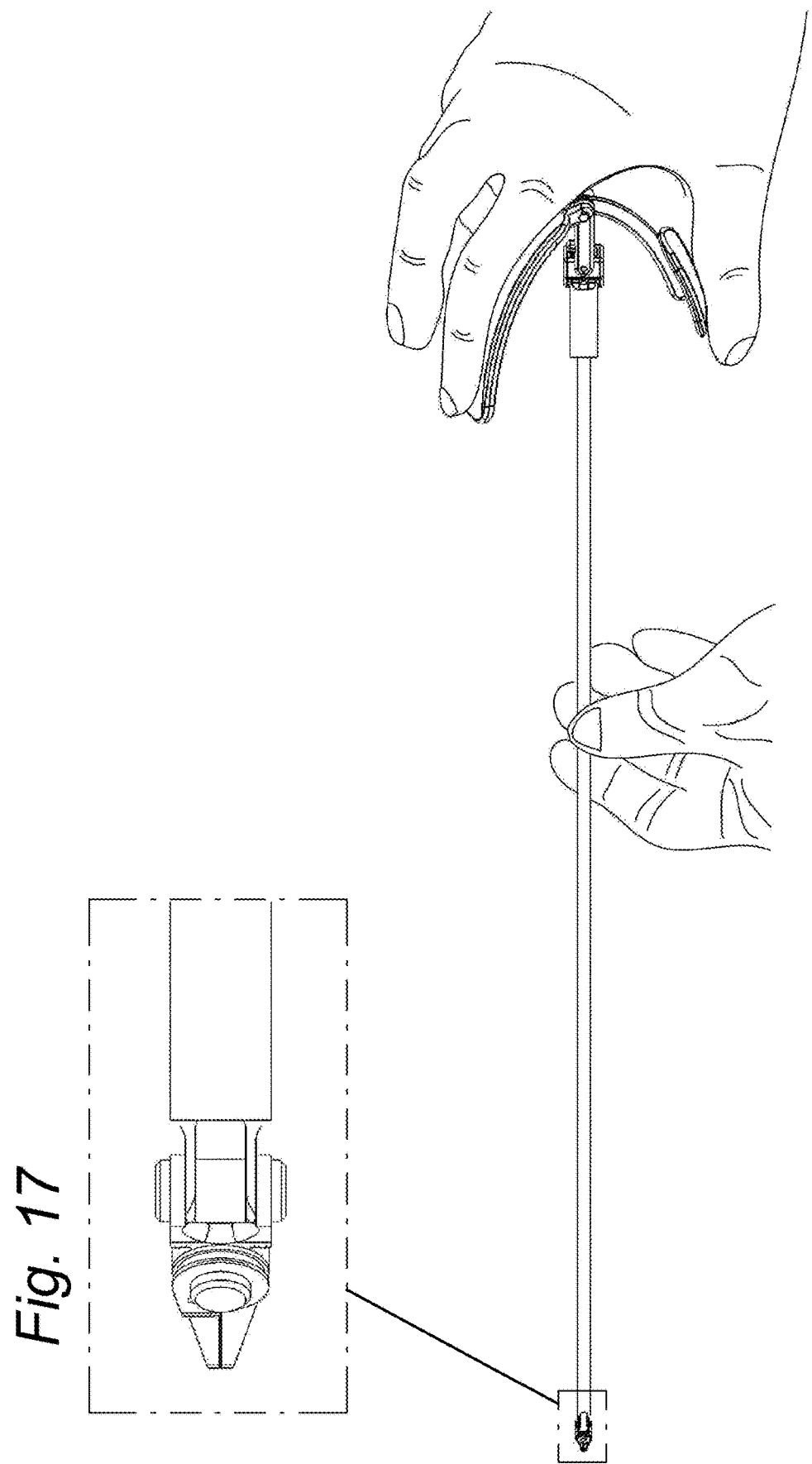
Figure 18:
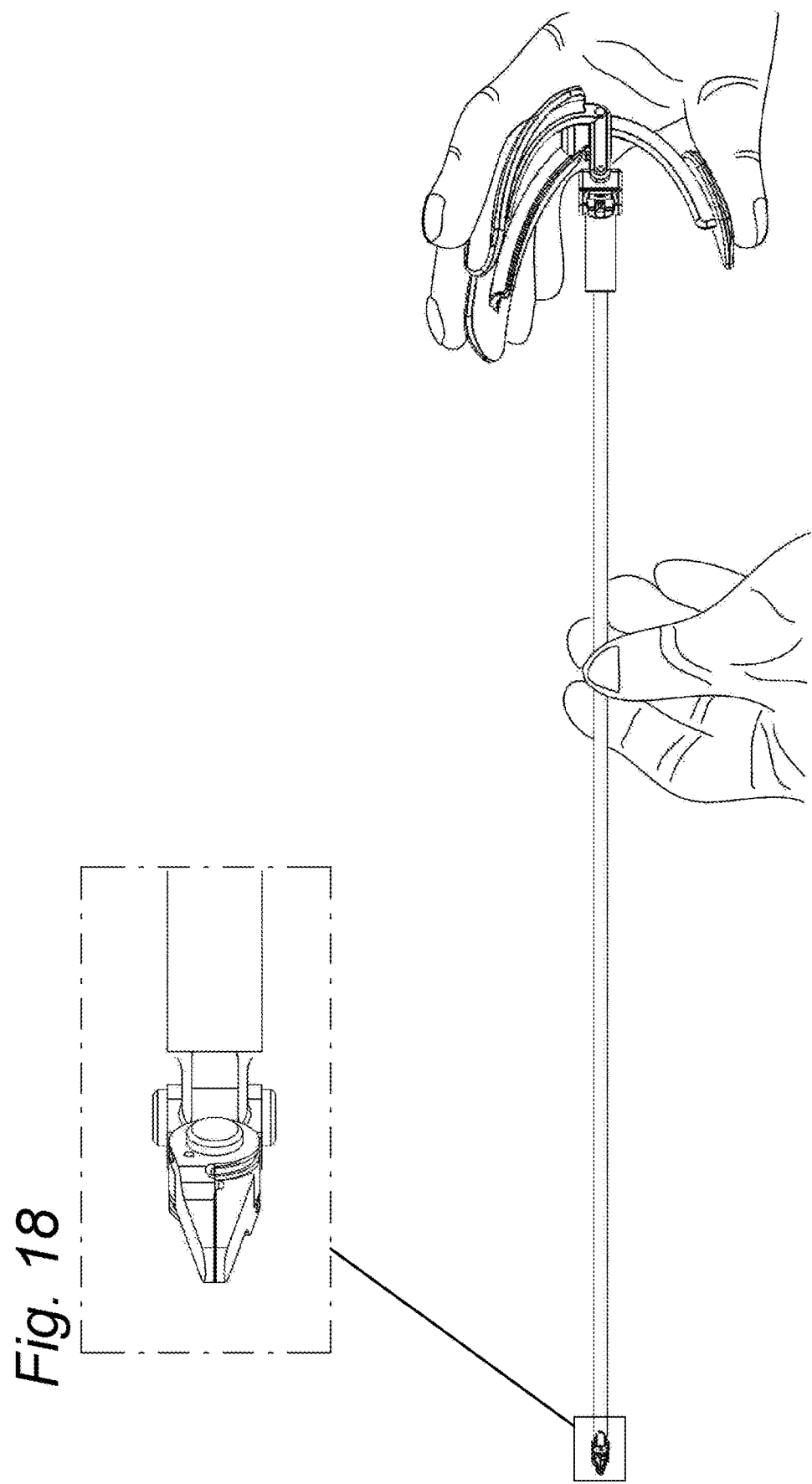

FIGS. 17 and 18 respectively show the hand movements for rotation of the jaws about the distal pitch axis by rotation of the handle 10 about the proximal pitch axis.

Even though the invention has been described in relation to a specific handle 10, it is envisaged that other types of handle may utilized such as scissor shaped handle or pistol grip handle. Alternatively, the present invention may be utilized in conjunction with automated actuators for instance under robotic control. Also the jaws 5,6 may be single acting or double acting, or may be replaced by alternative work members.

It is envisaged that for the distal and proximal end, any combination is possible for the capstans and bearing blocks, straight or crossing cables between pitch and pinch axis, straight or crossing cables along the shaft axis and straight or crossing cables between the pinch axis and pinch lever.

The invention claimed is:

1. A surgical instrument comprising:
   an elongate body with a longitudinal axis, having a distal end carrying a work member that is hingeable around a distal pitch axis and around a distal transverse axis, and a proximal end carrying a handle member having a finger support part and a thumb support part that are mutually attached in a hinge point and connected to the body via a hinging connection comprising
   a proximal pitch axis,
   a proximal pivot axis,
   a proximal pinch curved-surface cable actuating device and a proximal pivot curved-surface cable actuating device both rotatable about the proximal pivot axis and in relation to the proximal pitch axis, and
   a pinch lever rotatable about a hinge point axis, the pinch lever being connected to the proximal pinch curved-surface cable actuating device,
   the finger support part being curved and configured to support fingers of a user, the thumb support part being configured to support a thumb of the user, the finger and thumb support parts defining a gripping area each with a fingertip region near respective free ends of the finger and thumb support parts and an inside hand region near the hinge point that, in use, is disposed between the joint of the thumb and an index finger of the fingers of the user,
   wherein the handle member is configured to pivot around the proximal pitch axis, thereby pivoting the work member around the distal pitch axis,
   the handle member is configured to pivot around the proximal pivot axis, thereby pivoting the work member around the distal transverse axis, and
   the hinging connection that includes the proximal pitch axis and the proximal pivot axis is situated in the inside hand region, the proximal pitch axis being more proximal than free ends of the finger and thumb support parts that are spaced at a distance from the hinge point, the hinge point being more proximal than the proximal pitch axis and the proximal pivot axis of the hinging connection.

2. The surgical instrument according to claim 1, wherein the finger and thumb support parts are attached to the proximal end of the elongate body via an arm extending from the hinge point to the hinging connection.

3. The surgical instrument according to claim 1, wherein the finger support part comprises an index finger support part and situated adjacent thereto an additional finger support part configured to support at least one additional finger.

4. The surgical instrument according to claim 1, further comprising a pitch capstan having an axis transverse to the longitudinal axis at one end of the elongate body and a support rotatably mounted on the pitch capstan, the support carrying a transverse capstan having an axis transverse to the longitudinal axis and to the distal pitch axis,
   wherein the work member comprises two work elements movable relative to one another around the transverse axis of the transverse capstan connected to the support, at least two pairs of cables extending along the elongate body, along the distal pitch axis to a respective one of the work elements to which the respective cables are attached, the cables being guided in sliding contact along the pitch capstan situated at or near the distal pitch axis, the cables crossing from one side of a lateral plane defined by the longitudinal axis and the distal pitch axis to the other side of said plane, when going from a position on the distal pitch axis to a position on the work member.

5. The surgical instrument according to claim 4, wherein the slide bearing comprises the pitch capstan.

6. The surgical instrument according to claim 5, wherein the pitch capstan comprises a bushing laterally displaceable relative to the distal pitch axis.

7. The surgical instrument according to claim 6, wherein the proximal pitch axis is situated at a proximal end of the elongate body, the work member comprising the handle member with the finger and thumb support parts defining the gripping area having the fingertip region configured to support end parts of the fingers of the user and the inside hand region near the joint of the fingers and the thumb of the user, the proximal pitch axis being situated nearer to the inside hand region than to the fingertip region when seen along the longitudinal axis.

8. The surgical instrument according to claim 6, wherein the elongate body comprises a tensioning device configured to displace the distal pitch axis along the longitudinal axis.

9. The surgical instrument according to claim 5, wherein the proximal pitch axis is situated at a proximal end of the elongate body, the work member comprising the handle member with the finger and thumb support parts defining the gripping area having the fingertip region configured to support end parts of the fingers of a user and the inside hand region near the joint of the fingers and the thumb of the user, the proximal pitch axis being situated nearer to the inside hand region than to the fingertip region when seen along the longitudinal axis.

10. The surgical instrument according to claim 5, wherein the elongate body comprises a tensioning device configured to displace the distal pitch axis along the longitudinal axis.

11. The surgical instrument according to claim 4, wherein the pitch capstan comprises a bushing that is laterally displaceable relative to the distal pitch axis.

12. The surgical instrument according to claim 11, wherein the proximal pitch axis is situated at a proximal end of the elongate body, the work member comprising the handle member with the finger and thumb support parts defining the gripping area having the fingertip region configured to support end parts of the fingers of the user and the inside hand region near the joint of the fingers and the thumb of the user, the proximal pitch axis being situated nearer to the inside hand region than to the fingertip region when seen along the longitudinal axis.

13. The surgical instrument according to claim 11, wherein the elongate body comprises a tensioning device configured to displace the distal pitch axis along the longitudinal axis.

14. The surgical instrument according to claim 4, wherein the slide bearing comprises a block having a central passage extending around the distal pitch axis, and on each side of the lateral plane defined by the longitudinal axis and the distal pitch axis, two cable passages extending in the direction of the longitudinal axis.

15. The surgical instrument according to claim 14, wherein the proximal pitch axis is situated at a proximal end of the elongate body, the work member comprising the handle member with the finger and thumb support parts defining the gripping area having the fingertip region configured to support end parts of the fingers of the user and the inside hand region near the joint of the fingers and the thumb of the user, the proximal pitch axis being situated nearer to the inside hand region than to the fingertip region when seen along the longitudinal axis.

16. The surgical instrument according to claim 14, wherein the elongate body comprises a tensioning device configured to displace the distal pitch axis along the longitudinal axis.

17. The surgical instrument according to claim 4, wherein the proximal pitch axis is situated at a proximal end of the elongate body, the work member comprising the handle member with the finger and thumb support parts defining the gripping area having the fingertip region configured to support end parts of the fingers of the user and the inside hand region near the joint of the fingers and the thumb of the user, the proximal pitch axis being situated nearer to the inside hand region than to the fingertip region when seen along the longitudinal axis.

18. The surgical instrument according to claim 4, wherein the elongate body comprises a tensioning device configured to displace the distal pitch axis along the longitudinal axis.

19. The surgical instrument according to claim 2, wherein the finger support part comprises an index finger support part and situated adjacent thereto an additional finger support part configured to support at least one additional finger.

20. The surgical instrument according to claim 1, wherein the finger and thumb support parts extend toward the distal end from the hinge point.

* * * * *